United States Patent

Uji et al.

(10) Patent No.: US 9,820,650 B2
(45) Date of Patent: Nov. 21, 2017

(54) IMAGE PROCESSING APPARATUS AND IMAGE PROCESSING METHOD

(71) Applicant: CANON KABUSHIKI KAISHA, Tokyo (JP)

(72) Inventors: Akihito Uji, Kyoto (JP); Shigeta Arichika, Kyoto (JP); Hiroshi Imamura, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 239 days.

(21) Appl. No.: 14/182,656

(22) Filed: Feb. 18, 2014

(65) Prior Publication Data

US 2014/0240667 A1 Aug. 28, 2014

(30) Foreign Application Priority Data

Feb. 28, 2013 (JP) ................. 2013-040040

(51) Int. Cl.
*A61B 3/14* (2006.01)
*A61B 3/00* (2006.01)
*A61B 3/12* (2006.01)
*G06T 7/00* (2017.01)
*A61B 3/10* (2006.01)

(52) U.S. Cl.
CPC .......... *A61B 3/1241* (2013.01); *A61B 3/0025* (2013.01); *A61B 3/14* (2013.01); *G06T 7/0012* (2013.01); *A61B 3/1025* (2013.01); *G06T 2207/30041* (2013.01)

(58) Field of Classification Search
CPC .............................. A61B 3/1241; A61B 3/14
USPC ................................................. 351/206, 246
See application file for complete search history.

(56) References Cited

U.S. PATENT DOCUMENTS

| | | |
|---|---|---|
| 4,425,924 A | 1/1984 | Riva et al. |
| 6,588,901 B1 | 7/2003 | Grinvald et al. |
| 8,602,556 B2 | 12/2013 | Imamura |
| 2006/0147897 A1 | 7/2006 | Grinvald et al. |
| 2008/0247622 A1 | 10/2008 | Aylward et al. |
| 2008/0312533 A1 | 12/2008 | Balberg et al. |
| 2011/0137157 A1 | 6/2011 | Imamura et al. |
| 2012/0063660 A1 | 3/2012 | Imamura et al. |
| 2012/0063663 A1 | 3/2012 | Kawasaki |
| 2012/0130270 A1 | 5/2012 | Imamura et al. |
| 2012/0194782 A1 | 8/2012 | Imamura |
| 2012/0218517 A1 | 8/2012 | Imamura |
| 2013/0058553 A1 | 3/2013 | Yonezawa et al. |
| 2013/0265543 A1 | 10/2013 | Iwase et al. |

(Continued)

FOREIGN PATENT DOCUMENTS

| | | |
|---|---|---|
| EP | 2 455 912 A1 | 5/2012 |
| JP | 2008-104628 A | 5/2008 |
| JP | 2012-176095 A | 9/2012 |

OTHER PUBLICATIONS

Akihito Uji, "Observation of dark tail in diabetic retinopathy uising adaptive optics scanning laser ophthalmoscope", Proceedings of the 66th Annual Congress of Japan Clinical Ophthalmology, 2012, p. 27.

(Continued)

*Primary Examiner* — Jack Dinh
(74) *Attorney, Agent, or Firm* — Fitzpatrick, Cella, Harper & Scinto

(57) ABSTRACT

An image processing apparatus obtains a moving image of an eye area, identifies a region of blood cells in the obtained moving image, and determines the number of determined regions of blood cells.

18 Claims, 12 Drawing Sheets

(56) References Cited

U.S. PATENT DOCUMENTS

2014/0085606 A1     3/2014   Miyasa et al.
2014/0240669 A1     8/2014   Imamura

OTHER PUBLICATIONS

May 26, 2014 European Search Report in European Patent Appln. No. 14156223.1.
May 27, 2014 European Search Report in European Patent Appln. No. 14156225.6.

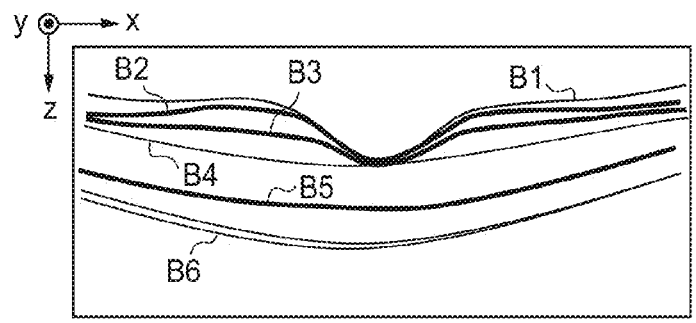
F I G. 6A
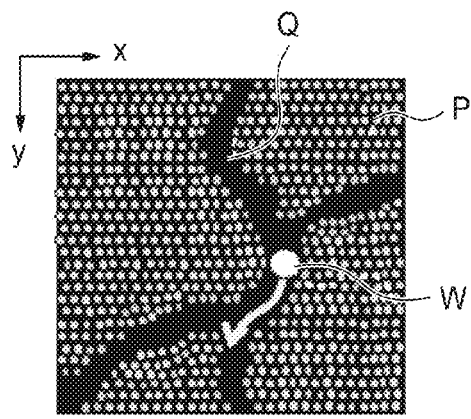
F I G. 6B
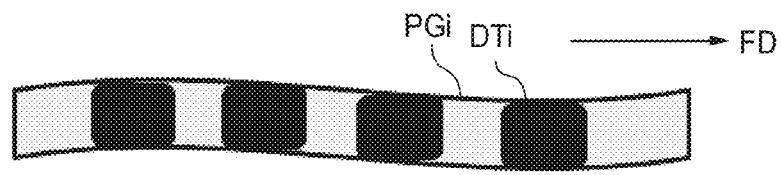
F I G. 6C
F I G. 6D

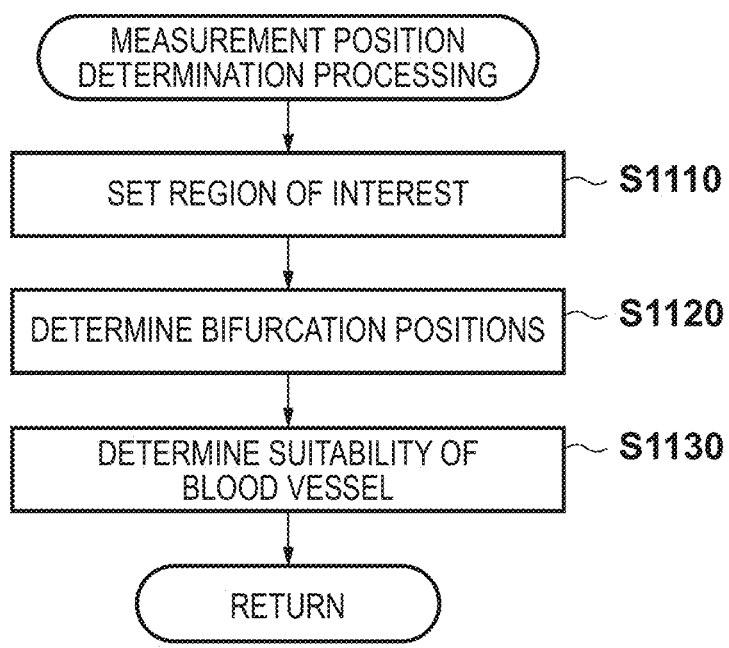

IMAGE PROCESSING APPARATUS AND IMAGE PROCESSING METHOD

BACKGROUND OF THE INVENTION

Field of the Invention

The present invention relates to an image processing apparatus and an image processing method used for ophthalmological consultations.

Description of the Related Art

Ophthalmic examinations are widely performed for the purpose of early diagnosis of lifestyle-related diseases and diseases that rank highly among causes of loss of eyesight. A scanning laser ophthalmoscope (SLO), which is an image processing apparatus that uses the principle of a confocal laser microscope, is an apparatus that performs Raster scanning of an eye fundus using a laser as a measuring beam and obtains a planar image at a high resolution and a high speed based on the intensity of the return light. The apparatus that captures this planar image will be referred to as an SLO apparatus, and the planar image will be referred to as an SLO image below.

In recent years, it has been possible to obtain a retinal SLO image with an improved horizontal resolution by increasing the diameter of the measuring beam in the SLO apparatus. However, there has been a problem in acquiring a retinal SLO image in that increasing the diameter of the measuring beam is accompanied by a decrease in the S/N ratio and the resolution of the SLO image due to aberrations in the eye of the examination subject.

In order to resolve the above-mentioned problem, an adaptive optics SLO apparatus has been developed that has an adaptive optics system that measures aberrations in the eye of the examination subject in real-time using a wavefront sensor and corrects aberrations of a measuring beam or its return light that occur in the examination subject eye using a wavefront compensation device, thereby enabling the acquisition of an SLO image with a high horizontal resolution.

This SLO image having a high horizontal resolution can be obtained as a moving image, and in order to observe blood flow dynamics for example in a non-invasive manner, retinal blood vessels are extracted from the frames of the moving image, and the movement speed and the like of blood cells in capillaries are subsequently measured. Also, in order to evaluate the relationship between the photoreceptor cells and the visual function using the SLO image, photoreceptor cells P are detected, and subsequently the density distribution and the alignment of the photoreceptor cells P are measured. FIG. 6B shows an example of an SLO image with a high horizontal resolution. The photoreceptor cells P, a low luminance region Q that corresponds to the position of a capillary, and a high-luminance region W that corresponds to the position of a leukocyte can be observed.

In the case of observing the photoreceptor cells P, measuring the distribution of photoreceptor cells P, or the like using the SLO image, the focus position is set near the outer layer of the retina (B5 in FIG. 6A) and an SLO image such as FIG. 6B is captured. On the other hand, there are retinal blood vessels and bifurcated capillaries in the inner layers of the retina (B2 to B4 in FIG. 6A). FIG. 6A shows an example of the various layers in the retina, from the inner limiting layer B1 to a pigmented layer B6. 45% of the blood that exists in blood vessels is composed of blood cell components, and of those blood cell components, about 96% are erythrocytes and about 3% are leukocytes. An erythrocyte has a diameter of about 8 μm, and a neutrophil, which is the most common type of leukocyte, is 12 to 15 μm in size.

With lifestyle-related diseases and systemic diseases such as diabetes, it is known that symptoms appear which indicate a decrease in blood fluidity (the extent to which blood flows smoothly). Specific examples of this include a decrease in blood cell deformability, and erythrocytes and thrombocytes tending to aggregate. In blood vessels, erythrocytes are constantly aggregated here and there as shown in FIG. 6C (which also shows flow direction FD), and erythrocyte aggregates DTi are formed. If the focus position is set to the photoreceptor cells and an SLO image having a high horizontal resolution is obtained, shadows will form in the vicinity of the photoreceptor cells since incident light does not pass through the erythrocytes, and an erythrocyte aggregate DTi is rendered as a dark tail DTi. On the other hand, if the blood returns to the normal state, for example, due to medical treatment, it is conceivable that the number of erythrocyte aggregates that are constantly aggregated as shown in FIG. 6D will gradually decrease. Conventionally, the number of erythrocyte aggregates flowing in blood vessels and their change over time could not be measured in a non-invasive manner.

A conventional technique of generating a spatiotemporal image for a capillary branch region in an adaptive optics SLO moving image and of measuring the degree of physiological erythrocyte aggregation based on the change in the length of an erythrocyte aggregate in the spatiotemporal image is disclosed in "Uji, Akihito, 'Observation of dark tail in diabetic retinopathy using adaptive optical scanning laser ophthalmoscope', Proceedings of the 66th Annual Congress of Japan Clinical Ophthalmology, p.27 (2012)" as a technique for measuring blood fluidity in a non-invasive manner.

However, in the above-described technique, the degree of erythrocyte aggregation that (temporarily) appears physiologically is measured based on the change in the length of the erythrocyte aggregate, and no technique of measuring the distribution (number according to region) of (constant) erythrocyte aggregates caused by abnormal erythrocyte aggregation that appears here and there in the blood vessel is disclosed.

SUMMARY OF THE INVENTION

An embodiment of the present invention provides an image processing apparatus and an image processing method that enable non-invasive measurement of blood fluidity based on the number of blood cell aggregates.

According to one aspect of the present invention, there is provided an information processing apparatus comprising: image obtaining unit configured to obtain a moving image of an eye area; unit configured to identify at least one region of blood cells in the obtained moving image; and determining unit configured to determine the number of identified regions of blood cells.

According to another aspect of the present invention, there is provided an information processing method comprising: an image obtaining step of obtaining a moving image of an eye area; an identification step of identifying a region of blood cells in the obtained moving image; and a determination step of determining the number of identified regions of blood cells.

Features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

FIGS. 6A to 6D are diagrams for describing images acquired in an embodiment and blood cell dynamics.

FIG. 11 is a flowchart showing measurement position determination processing according to the second to fourth embodiments.

DESCRIPTION OF THE EMBODIMENTS

Preferred embodiments of the image processing apparatus and method according to the present invention will be described below in accordance with the accompanying drawings. Note that the present invention is not limited to the embodiments disclosed below.

First Embodiment

An image processing apparatus according to the present embodiment is configured such that the number of blood cell aggregates in a single capillary branch in an SLO image selected by a user is measured and the measured value is displayed. Specifically, the image processing apparatus extracts a blood vessel from an SLO image Di that was obtained as a moving image, and a measurement target capillary branch is specified manually. Then, the number of blood cell aggregates is measured based on the number of blood cell aggregate paths in a spatiotemporal image generated along the specified capillary branch, and a normal value range is displayed along with the measured values.

Overall Configuration

Figure 2:
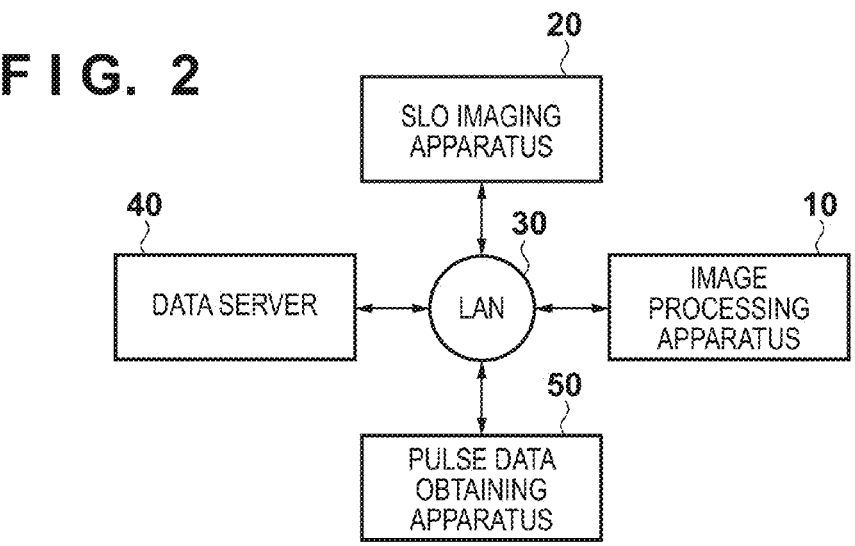
FIG. 2 is a block diagram showing an example of a functional configuration of a system that includes the image processing apparatus according to an embodiment.

FIG. 2 is a diagram showing a configuration of a system that includes an image processing apparatus 10 according to the present embodiment. The image processing apparatus 10 is connected to an SLO imaging apparatus 20, a data server 40, and a pulse data obtaining apparatus 50 via a local area network (LAN) 30 configured by an optical fiber, a USB, an IEEE 1394, or the like. Note that a configuration is possible in which these devices are connected via an external network such as the Internet, and an alternative configuration is possible in which the image processing apparatus 10 is directly connected to the SLO imaging apparatus 20, the data server 40, and the pulse data obtaining apparatus 50.

The SLO imaging apparatus 20 is an apparatus that captures the SLO image Di and transmits information regarding the obtained SLO image Di and a fixation target position Fi that is used at the time of imaging to the image processing apparatus 10 and the data server 40.

Note that if the SLO image Di is obtained at a different magnification in the present specification, it will be denoted as Dsi. That is to say, s is a variable indicating magnification and i is a variable indicating imaging position number, and they are expressed as s=1, 2, . . . , smax and i=1, 2, . . . , imax. As s increases, the imaging magnification increases (angle of view decreases). Note that in the present embodiment, a low-resolution SLO image and fixation target position where s=1 have one imaging position, and in the present specification, there are cases where they are written as D1 and F1 respectively.

The pulse data obtaining apparatus 50 is an apparatus that obtains biological signal data that changes autonomically, and is composed of a pulse wave meter or an electrocardiograph, for example. The pulse data obtaining apparatus 50 obtains pulse data while obtaining an SLO image Dsi according to an operation by an operator (not shown). Here, the pulse data is expressed as a sequence of points having the obtainment time t on one axis and the signal value measured by the pulse data obtaining apparatus 50 on the other axis. The obtained pulse data is transmitted to the image processing apparatus 10 and the data server 40.

The data server 40 holds the SLO images Dsi of the examination subject eye, the fixation target positions Fsi that are used at the time of imaging, imaging condition data such as the pulse data, image characteristics of the eye area, registration parameter values for the SLO images Dsi, measured values regarding blood cell aggregate number, normal value range data for the measured values, and the like. Here, image characteristics for a capillary Q, a blood cell W, and retinal blood vessels are treated as image characteristics of the eye area in the present embodiment. Note that the SLO images Dsi and the fixation target positions Fsi that are used at the time of imaging are output by the SLO imaging apparatus 20. The pulse data is output from the pulse data obtaining apparatus 50. Also, image characteristics of the eye area, registration parameter values for the SLO images Dsi, and measured values regarding the blood cell aggregate size are output from the image processing apparatus 10. Also, in response to a request from the image processing apparatus 10, the data server 40 transmits the SLO images Dsi, the fixation target positions Fsi, the pulse data, the eye area image characteristics, the registration parameter values, the measured values, and the normal value range data for the measured values to the image processing apparatus 10.

Figure 1:
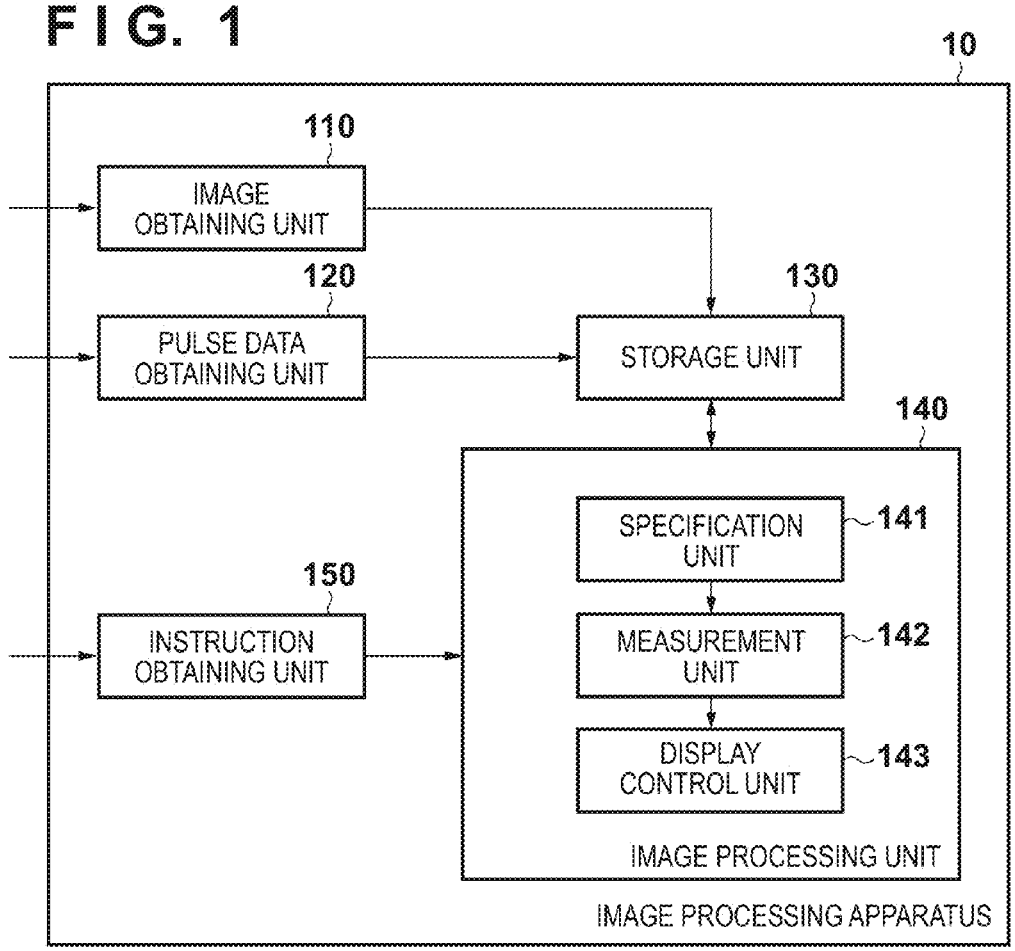
FIG. 1 is a block diagram showing an example of a functional configuration of an image processing apparatus according to a first embodiment.

A functional configuration of the image processing apparatus 10 according to the present embodiment will be described next with reference to FIG. 1. FIG. 1 is a block diagram showing the functional configuration of the image processing apparatus 10, and the image processing apparatus 10 has an image obtaining unit 110, a pulse data obtaining unit 120, a storage unit 130, an image processing unit 140, and an instruction obtaining unit 150. Also, the image processing unit 140 includes a specification unit 141, a measurement unit 142, and a display control unit 143.

Figure 3:
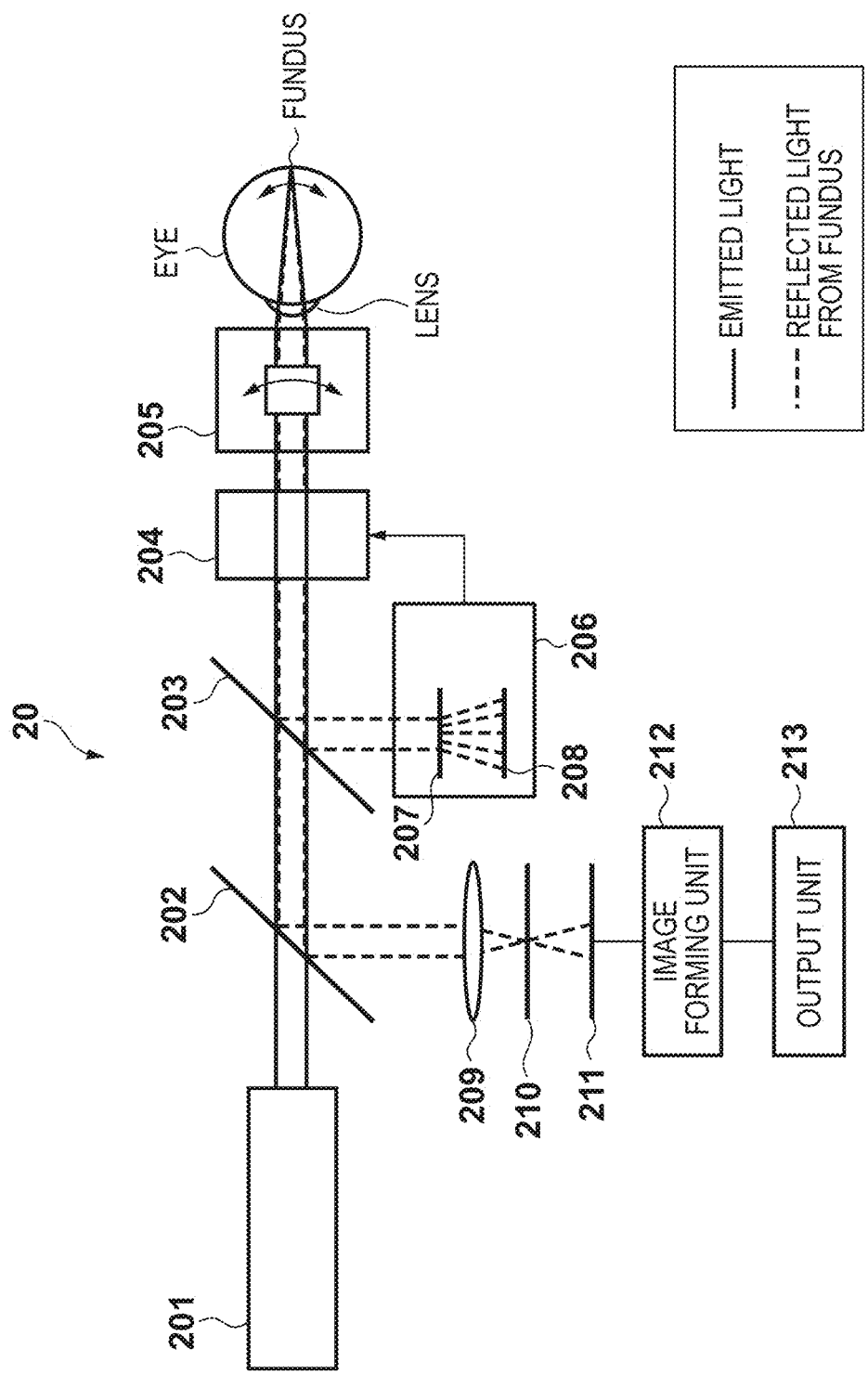
FIG. 3 is a diagram showing a configuration of an SLO imaging apparatus according to an embodiment.

The configuration of an adaptive optics SLO (Adaptive Optics Scanning Laser Ophthalmoscope (AO-SLO)) will be described next with reference to FIG. 3. The AO-SLO 20 has an SLD (Super Luminescent Diode) 201, a Shack-Hartmann wavefront sensor 206, an adaptive optics system 204, beam splitters (202, 203), an X-Y scanning mirror 205, a focus lens 209, an aperture 210, a light sensor 211, an image forming unit 212, and an output unit 213.

Light that is emitted from the SLD 201, which is a light source, is reflected by the eye fundus, a portion of that light is input to the Shack-Hartmann wavefront sensor 206 via the second beam splitter 203, and the rest is input to the light sensor 211 via the first beam splitter 202. The Shack-Hartmann wavefront sensor 206 is a device for measuring eye aberrations and has a lens array 207 and a CCD 208. When incident light passes through the lens array 207, a cluster of light spots appears on the CCD 208, and a wavefront aberration is measured based on the shift in the positions of the projected light spots. The adaptive optics system 204 drives an aberration correction device (a deformable mirror or a space/light phase modulator) based on the wavefront aberration measured by the Shack-Hartmann wavefront sensor 206 and corrects the aberration. The light that has undergone aberration correction is received by the light sensor 211 via the focus lens 209 and the aperture 210. The scanning position on the eye fundus can be controlled by moving the X-Y scanning mirror 205, and data corresponding to time (number of frames/frame rate) and the imaging target region that was designated in advance by the operator is obtained. The data is transferred to the image forming unit 212, image deformities caused by variation in the scanning speed are corrected, luminance values are corrected, and image data (moving image or still image) is formed. The output unit 213 outputs the image data formed by the image formation unit 212. In order to set the focus to a specified depth position in the eye fundus, at least one of the following types of adjustment can be used: adjustment using an aberration correction device in the adaptive optics system 204, and adjustment performed by installing a focus adjustment lens (not shown) in the optical system and moving that lens.

Figure 4:
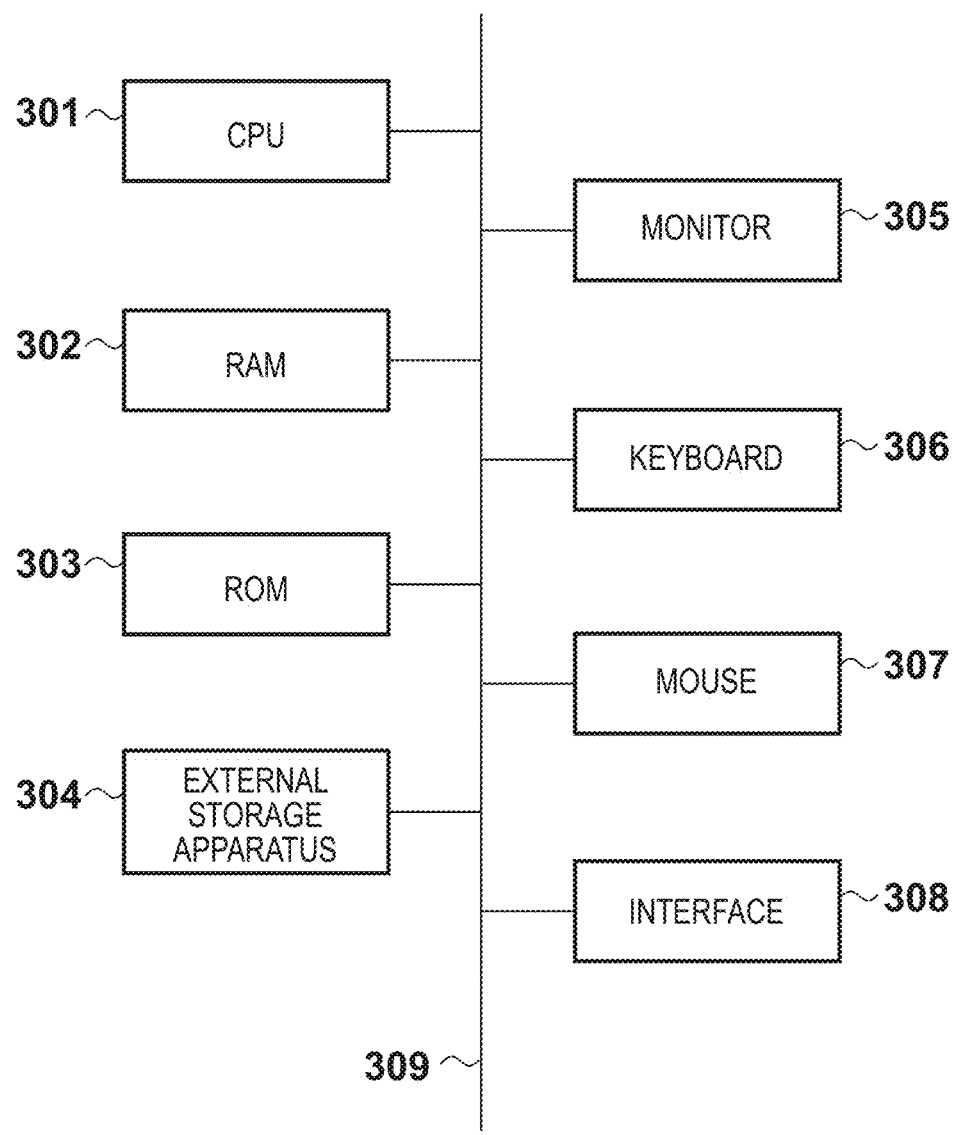
FIG. 4 is a block diagram showing an example of a hardware configuration of an image processing apparatus according to an embodiment.

A hardware configuration of the image processing apparatus 10 will be described next with reference to FIG. 4. In FIG. 4, reference numeral 301 is a central processing unit (CPU), reference numeral 302 is a memory (RAM), reference numeral 303 is a control memory (ROM), reference numeral 304 is an external storage apparatus, reference numeral 305 is a monitor, reference numeral 306 is a keyboard, reference numeral 307 is a mouse, and reference numeral 308 is an interface. The external storage apparatus 304 stores a control program for realizing an image processing function according to the present embodiment and data that is used when the control program is executed. The control program and the data are stored in the appropriate RAM 302 via a bus 309, are executed by the CPU 301, and function as the elements of the functional configuration shown in FIG. 1 under the control of the CPU 301.

Figure 5:
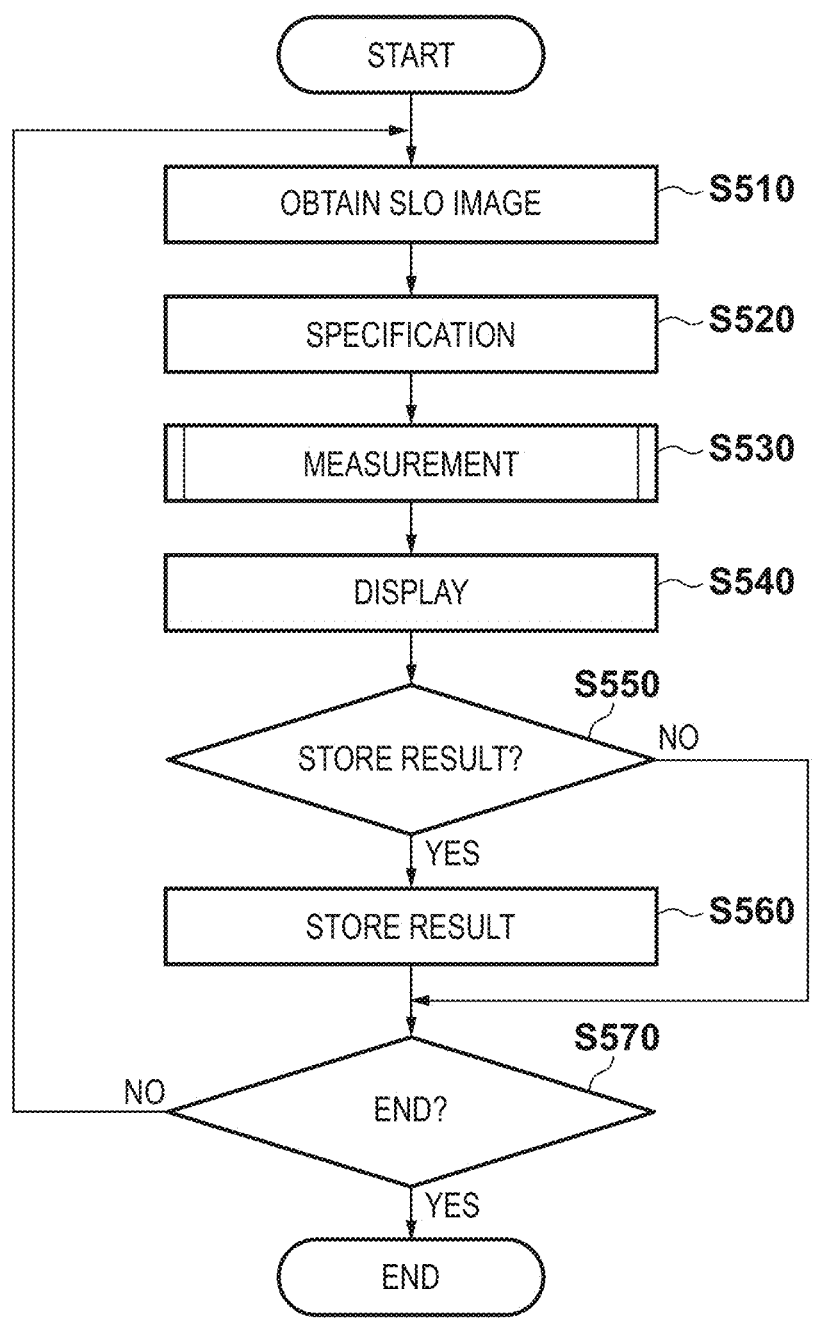
FIG. 5 is a flowchart of processing executed by the image processing apparatus according to the first embodiment.

Functions of the blocks that configure the image processing apparatus 10 shown in FIG. 1 will be described below in association with a specific execution procedure of the image processing apparatus 10 shown in the flowchart in FIG. 5.

Step S510

The image obtaining unit 110, which is an example of an image obtaining means for obtaining a moving image of an eye area, makes a request to the SLO imaging apparatus 20 to obtain an SLO image Dsi and a fixation target position Fsi. In the present embodiment, a low-magnification SLO image D1 is obtained by setting a fixation target position F1 to the fovea in the macular region, and a high-magnification SLO image D2i is obtained by setting a fixation target position F2i to the foveal and parafoveal regions. Note that the method for setting the imaging position is not limited to this, and a setting of any position may be used.

Also, the pulse data obtaining unit 120 makes a request to the pulse data obtaining apparatus 50 to obtain pulse data related to biological signals. In the present embodiment, a pulse wave meter is used as the pulse data obtaining apparatus, and pulse wave data is obtained from an earlobe of the examination subject. The pulse data obtaining apparatus 50 obtains the corresponding pulse data and transmits it in response to the acquisition request, and thereby the pulse data obtaining unit 120 receives the pulse wave data from the pulse data obtaining apparatus 50 via the LAN 30 and stores it in the storage unit 130.

Here, consideration will be given to the case where the image obtaining unit 110 starts to obtain the SLO images Dsi according to the phase of the pulse data obtained by the pulse data obtaining apparatus 50, and the case where the acquisition of the pulse data and the acquisition of the SLO images Dsi are started at the same time immediately subsequent to receiving a request to obtain the SLO images Dsi. In the present embodiment, a method is used in which the acquisition of the pulse data and the SLO images Dsi is started immediately subsequent to receiving a request to obtain the SLO images Dsi.

The SLO imaging apparatus 20 obtains the SLO images D1 and D2i and the fixation target positions F1 and F2i in response to the obtainment request and transmits them. The image obtaining unit 110 receives the SLO images D1 and D2i and the fixation target positions F1 and F2i from the SLO imaging apparatus 20 via the LAN 30. The image obtaining unit 110 stores the received SLO images D1 and D2i and the fixation target positions F1 and F2i in the storage unit 130. Note that in the present embodiment, the SLO images D1 and D2i are captured moving images whose focus positions have been set near to the photoreceptor cells and whose frames have been registered.

Step S520

The specification unit 141 performs specification of a vascular region (vascular region specification processing) in the retina from the SLO images D2i. In the present embodiment, the vascular region is specified in the SLO images D2i as the movement range of blood cell components using the following procedure.

(a) Perform subtraction processing between sequential frames of intermediate-scale images D2i whose frames have been registered (generate differential moving image).

(b) Calculate luminance value statistic (variance) for the frame direction at the x-y positions of the differential moving image generated in (a).

(c) Specify the region in which the luminance variance is at or above a threshold value Tv at the x-y positions of the differential moving image as the region in which blood cells are moving, or in other words, as the vascular region.

Note that the blood vessel detection processing is not limited to the method above, and any method may be used. For example, in (a) above, division processing for the luminance values between sequential frames may be used (generating a division moving image) instead of using subtraction. Alternatively, a blood vessel may be detected with the application of a filter that enhances linear structures in a specific frame of the SLO image D1 or the SLO images D2i. Note that the images obtained by specifying or identifying the vascular region out of the SLO images D2i are denoted below as the blood vessel images V2i.

Step S530

The measurement unit 142 is an example of a determining means for determining a region of blood cells in an obtained moving image, and a measuring means for measuring the number of the determined regions of blood cells. Although at least one of a blood cell, a blood cell aggregate, and a plasma region can be used as the region of blood cells, a blood cell aggregate is used in the present embodiment. Note that the plasma region is a region in a blood vessel that hardly includes any blood cells, it is identified using a blood cell aggregate, and it can be a measurement target region. In the present embodiment, the measurement unit 142 measures the number of blood cell aggregates as the number of regions of blood cells in a capillary branch in the SLO images D2i. Note that in the present embodiment, the user uses an interface such as a mouse to designate the measurement target capillary branch out of the vascular region specified in step S520. Note that the method for designating the capillary branch is not limited to this, and any publicly-known user interface may be used. The processing of the present step (blood cell aggregate number measurement) will be described in detail later with reference to the flowchart in FIG. 8.

Step S540

The display control unit 143, which is an example of a display control means, displays the measured value for the number of blood cell aggregates that was obtained in step S530, and a diagram generated based on that measured value on the monitor 305.

In the present embodiment, a graph (such as that shown in FIG. 12B) in which a normal value range has been plotted with the capillary branch number on the horizontal axis and the number of blood cell aggregates on the vertical axis is displayed as a graph indicating the number of blood cell aggregates with respect to the selected capillary branches by the display control means 143 in the SLO images D2i. FIG. 12B shows a display mode in which the above-mentioned measurement results are plotted, with the vascular branch (Vn) on the horizontal axis, and the measured number of blood cell aggregates (Nd) on the vertical axis. Note that in FIG. 12B, Ra is the abnormal value range, Rb is the border between the abnormal value range and the normal value range, Rn is the normal value range, and My is the number of blood cell aggregates measured in the vascular branch. Displaying the distribution of measured values in this way makes it possible easily to check whether or not there is a problem by comparing the number of blood cell aggregates with the normal value range. Note that the number of blood cell aggregates per pulse data cycle (or per second) at a specific position in the measurement target capillary branch (in the present embodiment, the central point of a vascular branch) is displayed as the measured values for the number of blood cell aggregates.

Note that the display control is not limited to this, and any kind of display may be performed as long as it is based on the measured values for the number of blood cell aggregates. For example, a distribution of numbers of blood cell aggregates, or a distribution of differences between the measured values for the number of blood cell aggregates and a statistical value (average value of measured values, or the like) may be displayed.

Step S550

The instruction obtaining unit 150 obtains an instruction from the exterior about whether or not to store the SLO images D1 and D2i, the fixation target positions F1 and F2i, pulse wave analysis data, the blood vessel images V2i, the measurement target positions, and measured values for the number of blood cell aggregates in the data server 40. This instruction is input by the operator via the keyboard 306 or the mouse 307 for example. If storage is instructed, the procedure moves to the processing of step S560, and if storage is not instructed, the procedure moves to step S570.

Step S560

The image processing unit 140 transmits the examination date/time, information for identifying the examination subject eye, the SLO images D1 and D2i, the fixation target positions F1 and F2i, the pulse wave analysis data, the blood vessel images V2i, the measurement target position, and measured values for the numbers of blood cell aggregates to the data server 40, where they are stored in association with each other.

Step S570

The instruction obtaining unit 150 obtains an instruction from the exterior (e.g. from an operator) regarding whether or not to end the processing related to the SLO images D2i performed by the image processing apparatus 10. This instruction is input by the operator via the keyboard 306 or the mouse 307. If an instruction to end processing is obtained, the processing ends. On the other hand, if an instruction to continue processing is obtained, the procedure returns to the processing of step S510 and processing for the next examination subject eye (or re-processing for the same examination subject eye) is performed.

Figure 8:
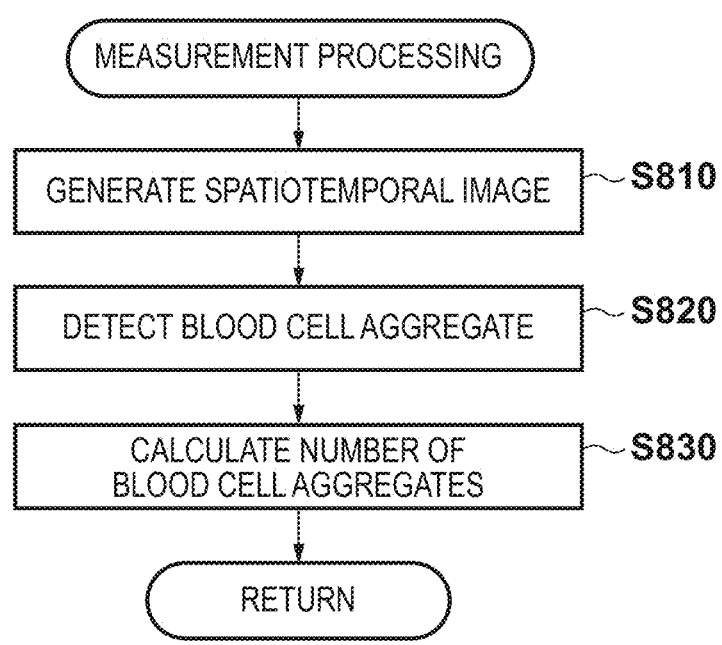
FIG. 8 is a flowchart showing measurement processing according to an embodiment.

The details of the measurement processing executed in step S530 will be described next with reference to the flowchart shown in FIG. 8.

Step S810

Figure 7A:
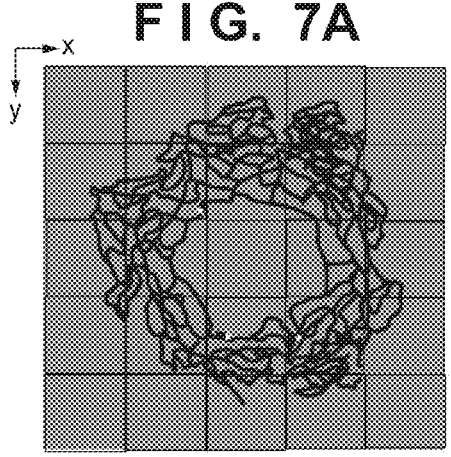
FIGS. 7A to 7F are diagrams for describing image processing contents according to an embodiment.
Figure 7B:
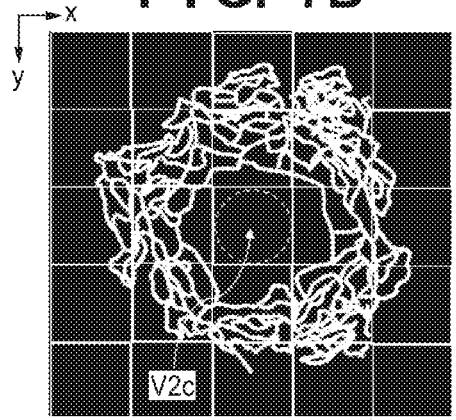
Figure 7C:
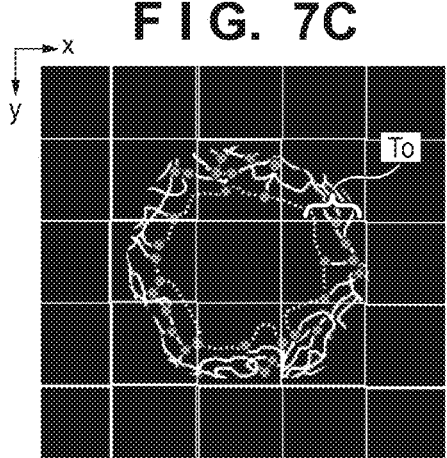
Figure 7D:
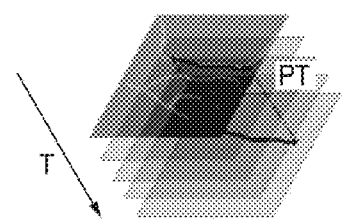
Figure 7E:
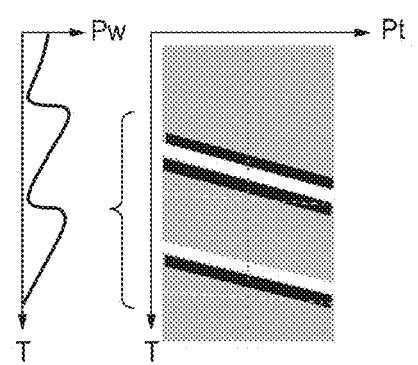
Figure 7F:
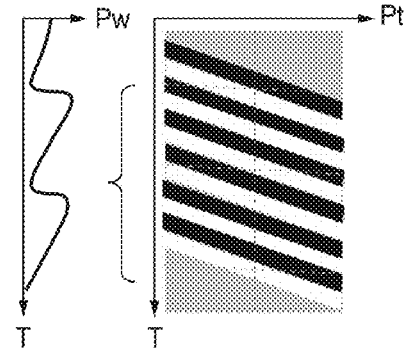

The measurement unit 142 generates a spatiotemporal image such as that shown in FIG. 7E or FIG. 7F with the vascular branch that was determined as the measurement target. The spatiotemporal image includes the position (Pt) in the vascular branch on its horizontal axis, the scanning time (T) on its vertical axis, and corresponds to the fact that a curved cross section (see FIG. 7D) of the SLO moving images (whose frames have been registered) is generated along the designated vascular branch. Note that the horizontal axis of the spatiotemporal image is set such that the side that is closer to the origin is the upstream side. The graphs in FIGS. 7E and 7F also show the pulse cycle Pw associated with the vascular branch position Pt and obtained by the pulse data obtaining apparatus 50.

The spatiotemporal image includes low-luminance linear components indicating the movement of erythrocyte aggregates, and high-luminance linear components (PGi in FIGS. 6C and 6D) indicating the movement of leukocytes or plasma regions (plasma regions that hardly contain any erythrocytes, also referred to as plasma-gaps).

Step S820

The measurement unit 142 determines a region of blood cells (a blood cell aggregate in the present example) in the specified vascular region (the specified vascular branch in the present example). The measurement unit 142 of the present embodiment detects a measurement target blood cell aggregate (DTi in FIGS. 6C and 6D) in the spatiotemporal image generated in step S810. In the present embodiment, since erythrocyte aggregates are present adjacent to plasma regions (plasma gaps) (or behind leukocytes), high-luminance movement paths are first detected in the spatiotemporal image and erythrocyte aggregates are detected by detecting dark tails adjacent to the high-luminance movement paths.

In other words, a location that is adjacent to a region having luminance values exceeding a first threshold value, and that has a luminance value that is lower than a second threshold value in the specified vascular region is determined as a region of blood cells. More specifically, line enhancement is performed using a publicly-known line enhancement filter, and the high-luminance path is subsequently detected by binarizing using a threshold value Tt1. Furthermore, the low-luminance blood cell aggregate path is detected by binarizing the dark tail adjacent to the detected high-luminance path using a threshold value Tt2. Note that the method for detecting the blood cell aggregate is not limited to the above-described method, and any image processing method may be used. Also, the movement path of the erythrocyte aggregate may be specified by directly detecting a dark tail using threshold value processing or the like.

Step S830

The measurement unit 142 measures the number of erythrocyte aggregate paths that were detected and selected in step S820. Here, since consideration is given to the influence of the heartbeat, the paths of erythrocyte aggregates that are present in phase sections corresponding to an integral multiple of pulse data cycles are selected as the measurement targets out of the detected erythrocyte aggregate paths. In the present embodiment, as shown in FIGS. 7E and 7F, erythrocyte aggregate paths that are included in phase sections corresponding to two cycles of pulse data Pw at the central point of a vascular branch (dotted line region in the vertical direction of the spatiotemporal image) are selected as the measurement targets. It is measured as 1.5 per cycle in FIG. 7E and 2.5 per cycle in FIG. 7F.

Note that the measurement unit 142 obtains pulse data corresponding to the SLO images D2i in advance from the storage unit 130 and detects the peak values of the pulse data. Also, the measured values for the number of blood cell aggregates may be calculated based on a value obtained by directly measuring the size of the blood cell aggregate in a frame of the video configured by the SLO images D2i without the spatiotemporal image being generated. Alternatively, rather than using a fixed number of cycles starting from the measurement start time, the number of erythrocyte aggregates in a section corresponding to a fixed number of seconds may be measured, and the number of blood cell aggregates per second may be measured.

According to the above configuration, the image processing apparatus 10 measures the number of blood cell aggregates (number of regions of blood cells) in a capillary branch that was determined manually, and displays the measured values. Accordingly, blood fluidity can be measured non-invasively based on the number of blood cell aggregates.

Second Embodiment

The first embodiment described a configuration in which the measurement target capillary branch is selected manually. The second embodiment will describe an image processing apparatus that automatically determines a capillary branch that is appropriate for measuring the number of blood cell aggregates and subsequently measures the number of blood cell aggregates in the capillary branch and displays the distribution of the measured values.

Specifically, a composite image is generated by compositing blood vessel images obtained by extracting blood vessels from the SLO images Dsi. The image processing apparatus 10 specifies a parafoveal region based on the shape of an avascular region detected in the composite blood vessel image and extracts vascular branch candidates by determining vascular bifurcation positions in the parafoveal region. Then, a measurement target vascular branch is specified based on the shapes of the extracted vascular branch candidates, the number of blood cell aggregates is measured based on the number of blood cell aggregate paths in the spatiotemporal image that was generated using the specified vascular branch, and the measured values are displayed as a map.

Figure 9:
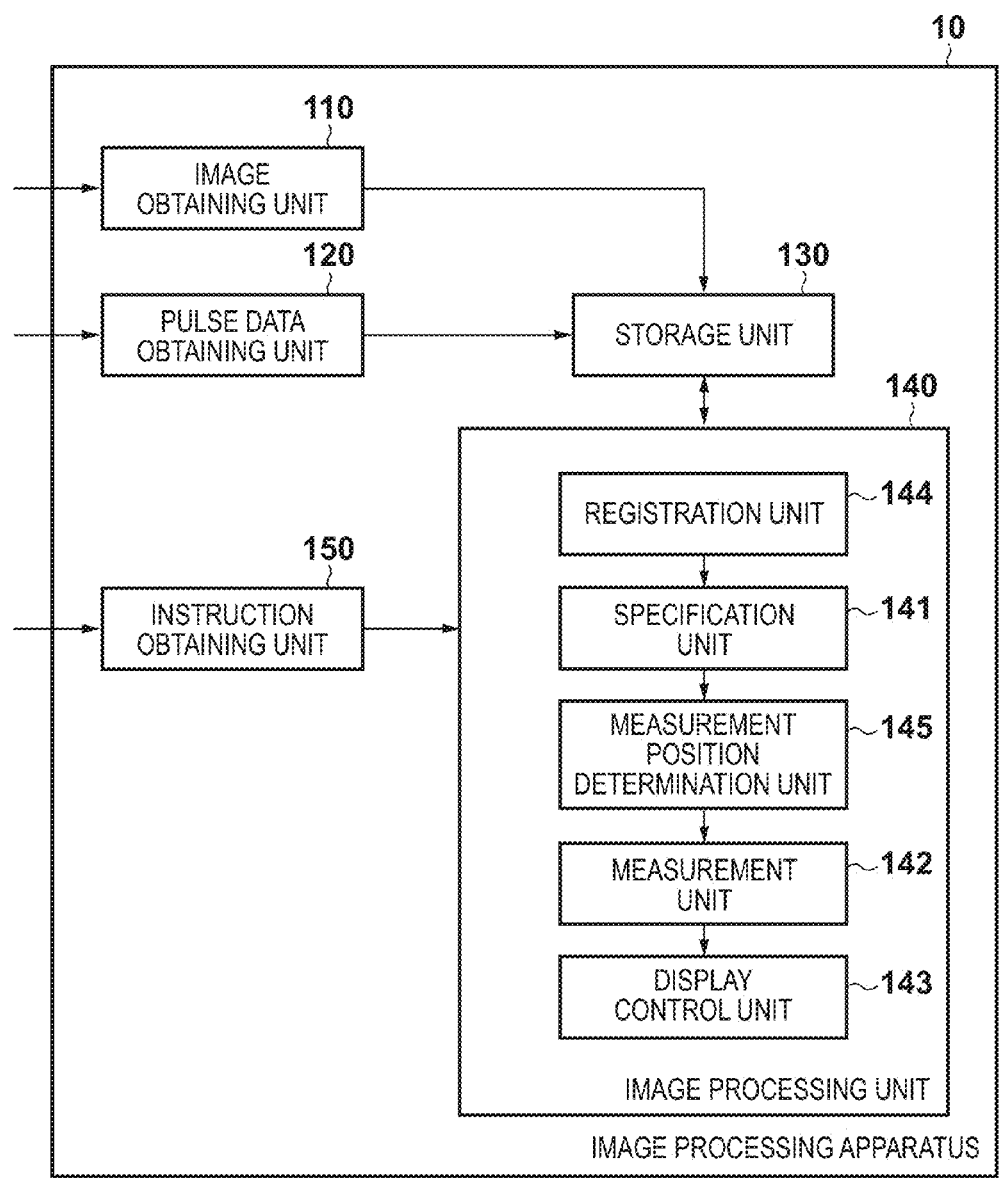
FIG. 9 is a block diagram showing an example of a functional configuration of an image processing apparatus according to second to fourth embodiments.

The configuration of devices that are connected to the image processing apparatus 10 according to the second embodiment is similar to that in the case of the first embodiment, and therefore the description will not be repeated. FIG. 9 shows functional blocks of the image processing apparatus 10. The image processing unit 140 differs from that of the first embodiment (FIG. 1) in that it includes a registration unit 144 and a measurement position determination unit 145.

Figure 10:
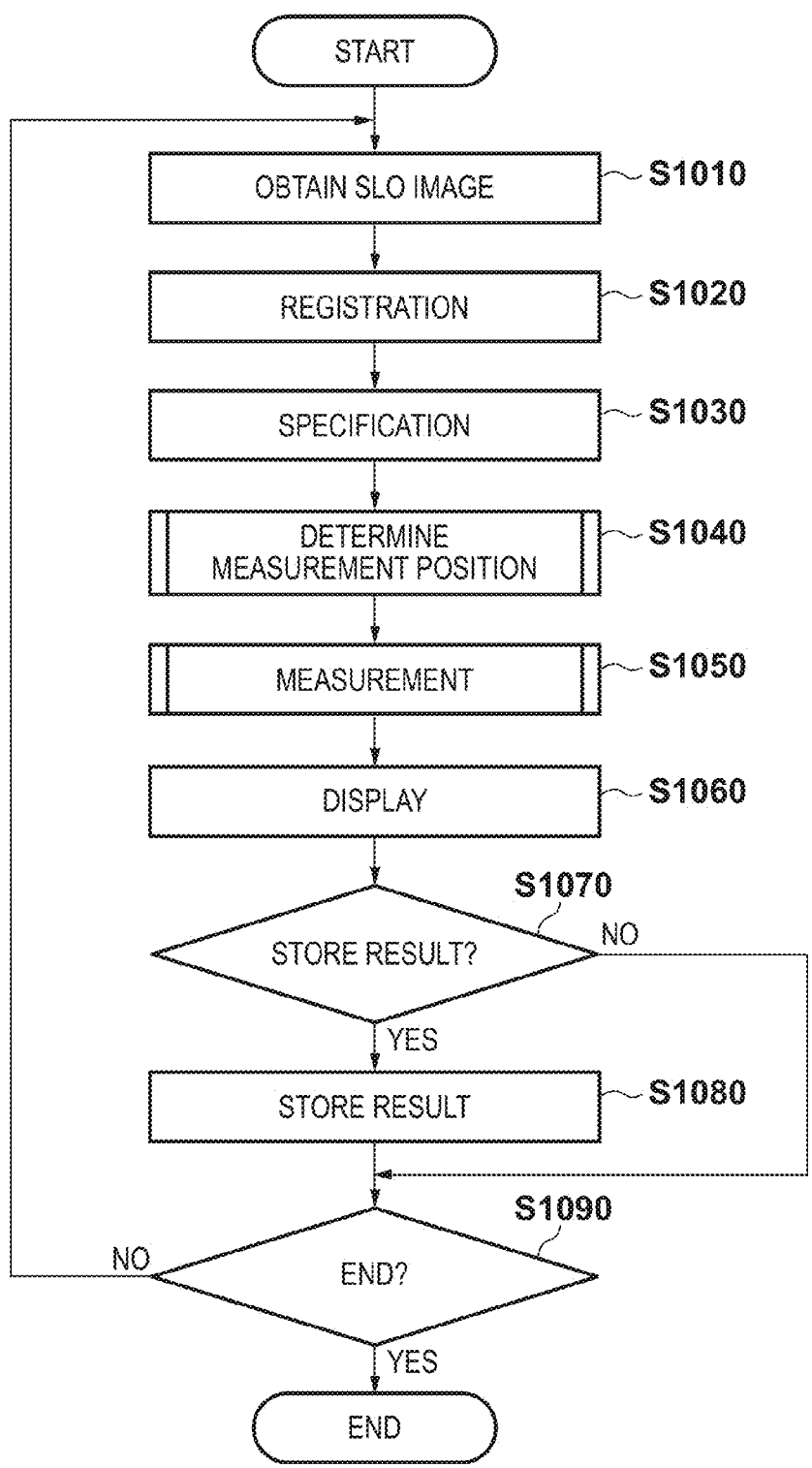
FIG. 10 is a flowchart of processing executed by the image processing apparatus according to the second to fourth embodiments.

Image processing executed by the image processing apparatus 10 according to the second embodiment will be described below with reference to the flowchart in FIG. 10. Note that the processing of steps S1010 and S1090 in FIG. 10 is the same as the processing of steps S510 and S570 in the first embodiment (FIG. 5), and the description will not be repeated.

Step S1020

The registration unit 144 registers the SLO image D1 and the SLO images D2i and obtains the relative positions of the SLO images D2i in the SLO image Dl. Note that if there is an overlapping region in the SLO images D2i, the degree of image similarity is first calculated for the overlapping region, and the positions of the SLO images D2i are registered at the position at which the degree of image similarity is the largest.

Also, if three or more SLO images with different magnifications are obtained in step S1010, registration is performed in sequence starting from the SLO image having the lowest magnification. For example, if the SLO image D1, the SLO images D2i, and SLO images D3i are obtained, registration between the SLO image D1 and the SLO images D2i is performed, and subsequently, registration between the SLO images D2i and the SLO images D3i is performed.

Note that the registration unit 144 obtains the fixation target positions F2i that is used at the time of capturing the SLO images D2i from the memory unit 130 and uses them as the initial points in the search for registration parameters in the registration between the SLO image D1 and the SLO images D2i. Also, any suitable method can be used as the method for image similarity degree and coordinate conversion, and in the present embodiment, registration is performed using a correlation coefficient for the degree of image similarity and Affine conversion is used as the coordinate conversion method.

The composite image of the SLO images D2i is generated using information regarding the relative positions of the SLO images D2i on the SLO image D1 that were obtained in the present step.

Step S1030

Processing that is basically similar to that of step S520 in the first embodiment is performed. That is to say that the specification unit 141 specifies a vascular region in the retina in the SLO images D2i. Also, the specification unit 141 generates a composite image of the blood vessel images V2i using the registration parameter values obtained in step S1020.

Step S1040

The measurement position determination unit 145 automatically determines a capillary branch that is to be the target for measuring the number of blood cell aggregates. The automatic determination includes information obtainment processing for obtaining the vascular diameters of multiple vascular branches that include multiple vascular bifurcations in the obtained moving image, and determination processing for determining vascular branches having vascular diameters that fall within a predetermined range among the multiple vascular branches as the measurement targets. The processing of the present step will be described in detail later with reference to the flowchart in FIG. 11.

Step S1050

The measurement unit 142 measures the number of blood cell aggregates by performing processing that is similar to that in steps S810 to S830 in the first embodiment. Also, in the second embodiment, a simple index suggesting a decrease in blood fluidity is calculated based on the value of the number of blood cell aggregates measured in the measurement target vascular branch. For example, "the percentage of the sum of the lengths of blood vessels containing a region of blood cells, or of blood vessels that do not contain a region of blood cells, with respect to the sum of the lengths of measurement target blood vessels" will be used as such an index. In other words:

(sum of lengths of measurement target vascular branches through which erythrocyte aggregates pass)/(sum of lengths of measurement target vascular branches)  (1)

or (sum of lengths of measurement target vascular branches through which erythrocyte aggregates do not pass)/ (sum of lengths of measurement target vascular branches)  (2)

is calculated. This index utilizes the fact that there are few vascular branches through which erythrocyte aggregates pass (vascular branches in which erythrocyte aggregates are present) in a healthy eye, and the fact that the number of vascular branches through which erythrocyte aggregates pass (number of vascular branches in which erythrocyte aggregates are present) increases as blood fluidity decreases. Index (1) increases and index (2) decreases as blood fluidity decreases.

Alternatively, "a value obtained by dividing the sum of the lengths of blood vessels that do not include regions of blood cells by the area of a region of interest" may be used as the above-described index. In other words:

(sum of lengths of measurement target vascular branches through which erythrocyte aggregates do not pass)/ (area of measurement target region (ROI))  (3)

may be calculated.

Index (3) not only reflects a decrease in blood fluidity, but also the progression of vascular obstruction. The smaller the value is, the more it indicates that the blood fluidity has decreased and vascular obstruction has progressed.

Note that the following method may be used as the method for measuring the number of blood cell aggregates in step S830. In other words, a blood cell aggregate path in the case where the pulse data is in a specific phase section is used as the measurement target, and a statistical value for the measured values is calculated. For example, the number of blood cell aggregates present in the vascular branches at multiple end-diastolic scanning times such as those indicated by the horizontal dotted lines in FIGS. 7E and 7F is measured and an average value and a variance are obtained. By using the average value, the measurement accuracy can be improved compared to the case of using a singular measurement value, and furthermore, the inverse of the variance value for example can be used as reliability degree for the measured values. Note that if the variance value is less than a threshold value Tc (or equal to 0), the largest pre-set value for reliability degree is allocated. In FIG. 7E, the average value for the number of blood cell aggregates is 1 and the variance is 0, and in FIG. 7F, the average value is $(2+2+1)/3 \approx 1.67$, and the variance is about 0.22.

Also, the measured value is not limited to the number of blood cell aggregates in the measurement target vascular branches, and a deviation from a normal value may be calculated based on a normal value range for the number of blood cell aggregates, for example.

Step S1060

The display control unit 143 displays the measured value for the number of blood cell aggregates that was obtained in step S1050, and a display mode generated based on that measured value on the monitor 305.

Figure 12A:
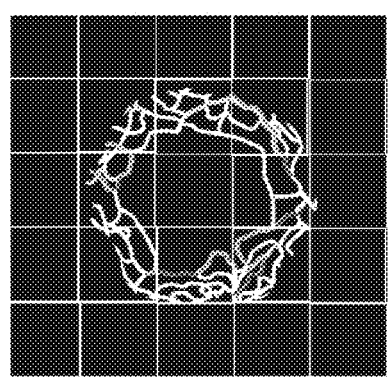
FIGS. 12A to 12D are diagrams for describing display contents regarding values measured in an embodiment.
Figure 12B:
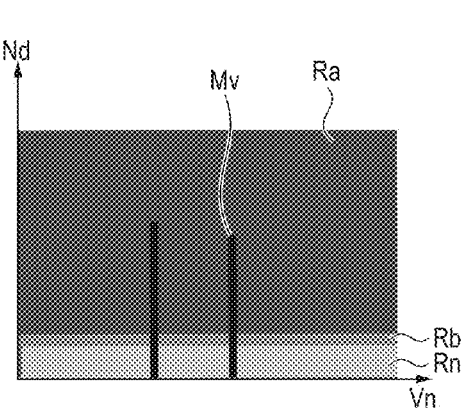

In the second embodiment, the display control unit 143 colorizes the measured values for the number of blood cell aggregates in the measurement target vascular branches determined in step S1040 and displays them as a map as shown in FIG. 12A. Accordingly, the distribution of measured values based on the number of blood cell aggregates can be listed and understood. Note that the method of displaying the distribution of measured values is not limited to a color display, and for example, it is possible to display them as density values, and they may be included as measured values as well. Also, the display control unit 143 displays an index (at least one of (1), (2), and (3)) calculated in step S1050.

Note that the measured value is not limited to the number of blood cell aggregates in the measurement target vascular branches, and a deviation from a normal value that is calculated based on a normal value range for the number of blood cell aggregates for example may be displayed as a map.

Also, similarly to the case of the first embodiment, a graph (such as that of FIG. 12B) in which a normal value range has been plotted with the vascular branch number (Vn) on the horizontal axis and the number of blood cell aggregates (or the average value or variance value of the number of blood cell aggregates) (Nd) on the vertical axis is displayed as a graph (Mv) indicating the number of blood cell aggregates with respect to the vascular branches that were designated by the user. This makes it possible to easily check whether or not there is a problem by comparing the measured number of blood cell aggregates with the normal value range. The number of blood cell aggregates that passed through in the section corresponding to the designated number of cycles of pulse data is converted into a measured value per cycle (or per second) and displayed as the measured value for the number of blood cell aggregates.

Furthermore, the display control unit 143 generates a superimposed image in which the SLO images D2i are superimposed on an SLO image D11 such as that shown in FIG. 7A based on the registration parameter values obtained in step S1020. Here, the playback timings of the SLO images D11 and D2i are synchronized based on the pulse data (cycle data based on a biological signal such as a pulse wave) and displayed. Specifically, the display control unit 143 obtains pulse data corresponding to the SLO images D11 and D2i from the pulse data obtaining unit 120, detects the respective peak values in the pulse data, and thereby calculates a beat cycle. Next, in order to deal with the case where the beat cycle is different between SLO images, adjustment processing for the display frame interval between the images (frame interpolation processing) is performed. Furthermore, by playing back an integer number of frames in a beat cycle, composite video display is performed. Note that in an image whose frames have been registered, there are cases where visibility is reduced due to regions having a pixel value of 0 appearing at the edge regions of the image, and therefore only pixels having pixel values greater than 0 are displayed in all frames at the time of composite display. If the pulse data has not been obtained, this step is not performed, and the moving image may undergo composite display without the playback start times being adjusted. The distribution of the number of blood cell aggregates can be understood quantitatively according to the map of the number of blood cell aggregates while the dynamics of the blood cell aggregates are understood intuitively according to the superimposed image.

Note that the display control is not limited to the description above, and any kind of display may be performed as long as it is based on the measured values for the number of blood cell aggregates.

Step S1070

The processing of the instruction obtaining unit 150 in the present step is basically similar to that of the first embodiment (step S550), but it is different from the first embodiment in that the instruction about whether or not to store the registration parameter values in the data server 40 is obtained from the exterior. If storage is instructed, the procedure moves to the processing of step S1080, and if storage is not instructed, the procedure moves to step S1090.

Step S1080

The processing performed by the image processing unit 140 in the present step is basically similar to that in the first embodiment (step S560), but it is different from the first embodiment in that the registration parameter values are also transmitted to the data server 40.

The details of the measurement position determination processing executed in step S1040 will be described next with reference to the flowchart shown in FIG. 11. In the present embodiment, vascular branch specification processing for specifying multiple vascular branches is executed using a region including two neighboring vascular bifurcations and a blood vessel between the two vascular bifurcations as one vascular branch, and the vascular branches at which vascular diameters are obtained by the information obtainment processing are specified automatically. The specification process is effectively the identification of particular aspects of the image, the particular aspect in this case being the vascular branch and the identification being performed by identifying first vascular bifurcations and then specifying a branch between the two bifurcations.

Step S1110

The measurement position determination unit 145 determines a region of interest (ROI) based on the vascular region obtained in step S1030. In the present embodiment, an ROI related to the parafovea is set. Specifically, the border of an avascular region is detected in the vascular region obtained in step S1030.

In the vicinity of the retinal fovea, a region in which there are no retinal blood vessels (an avascular region) is present (region enclosed by the uneven solid line in the central portion of the composite blood vessel image shown in FIG. 7B). It should be noted that the avascular region near the foveal may be referred to as (Foveal Avascular Zone) FAZ. There is a lot of individual variation in the shape of the avascular region border, and primary lesions in retinal blood vessels tend to appear in the periphery of the avascular region border. Capillaries belonging to the avascular region border are where vascular lesions appear particularly early, and there are cases where the avascular region border is used when the position of the fovea is to be determined. Accordingly, the avascular region border is important as a target of inspection and analysis.

In the present embodiment, in a blood vessel image V2c that is positioned in the center of FIG. 7B, the measurement position determining unit 145 arranges a deformable model (dotted-line portion in same drawing) that corresponds to the inscribed circle in the blood vessel image V2c on the composite image of the blood vessel images V2i. After deformation is complete, the deformable model is positioned on the avascular region border (dotted line portion in FIG. 7C). A position on the outside at a distance of a threshold value To from the avascular region border is determined using a distance image (image that has values of distance from the border in its pixel values) that is obtained by furthermore performing Euclidean distance conversion on the avascular region border. Although any value can be set as the threshold value To, it is generally set to around 150 (μm) for a healthy person, and therefore that value will be used in the present embodiment as well. As shown in FIG. 7C, an annular (donut-shaped) region of interest is determined using the two specified borders, namely an inner border and an outer border.

Note that in the second embodiment, the circular region at a distance of the threshold value To from the avascular region border was set as the region of interest, but the present invention is not limited to this. For example, it is possible to set only a capillary (dotted line in FIG. 7C) belonging to the avascular region border as the region of interest. This is because the capillary belonging to the avascular region border are where vascular lesions appear the earliest, and is a regions of interest at which measurement of the number of blood cell aggregates can be performed most readily.

Also, although the width of the annular region that is to be the region of interest was fixed at a threshold value To in the above-described embodiment, the present invention is not limited to this. For example, with a disease such as diabetic retinopathy, in which lesions appear in retinal capillaries in the parafovea, capillaries are obstructed as the disease progresses and the avascular region increases in size. Also, if the avascular region increases in size, vascular lesions may possibly occur in a range wider than the periphery of the avascular region. Therefore, a value obtained by multiplying a value that is proportional to the area of the avascular region to the threshold value To may be set as the distance from the avascular region border, and thereby the annular region of interest may be determined.

Step S1120

The measurement position determination unit 145 detects bifurcation positions in the vascular region in the region of interest that was set in step S1110. Since the number of blood cell aggregates for each vascular branch is displayed as shown in FIGS. 12A and 12B in the present embodiment, the positions of vascular bifurcations need to be specified. However, due to the fact that there are cases where a blood vessel appears to include a bifurcation when in actuality it is merely an intersection of two blood vessels, the bifurcation areas need to be specified after being distinguished from intersections.

Specifically, the measurement position determination unit 145 first performs thinning processing on the vascular region in the region of interest, and bifurcations are determined based on the continuity of white pixels (pixels having a non-zero pixel value) in the obtained binary image. In the present embodiment, if there are three white pixels among the pixels adjacent to the white pixel that is the determination target, it is determined as a bifurcation, and if there are four white pixels, it is determined as an intersection, and thereby the bifurcation positions as indicated by the round marks in FIG. 7C are determined.

Step S1130

Among the blood vessels in the region of interest, the measurement position determination unit 145 determines regions having the bifurcation positions determined in step S1120 at both ends as vascular branch candidates in the vascular images V2i. Next, vascular branch candidates that satisfy the following condition are determined as measurement target vascular branches.

The diameter (thickness) of the vascular branch candidate is less than a threshold value Tmax.

Here, the present condition is based on a constraint that if the vascular diameter is greater than the capillary diameter, many erythrocytes or blood cell aggregates will block incident light, and therefore they will always appear as dark tails (regardless of whether or not there is a blood cell aggregate), which makes it difficult to measure the number of blood cell aggregates. For example, it is preferable that the vascular diameter of the vascular branch is about 10 μm to about 20 μm due to the fact that the erythrocyte diameter is about 8 μm and that a neutrophil, which is the most common type of leukocyte, is 12 to 15 μm in size.

Note that the method for determining the measurement target vascular branch is not limited to this. For example, it is possible to use a condition that "the smallest luminance of a vascular branch that is in the same location throughout all of the frames calculated in step S530 is less than a threshold value Ts" as an additional condition for determining a measurement target vascular branch. This is a condition that is set in order to narrow down the number of capillary branches that the erythrocyte aggregates pass through, and it corresponds to the fact that a capillary branch is at its lowest luminance when an erythrocyte aggregate passes through it.

According to the above-described configuration, the image processing apparatus 10 automatically determines vascular branches that are appropriate for measuring the number of blood cell aggregates, subsequently measures the number of blood cell aggregates in the vascular branches, and displays a distribution of the measured values. Accordingly, after a measurement target vascular branch is specified in a simple manner, blood fluidity can be measured non-invasively.

Third Embodiment

The image processing apparatus according to a third embodiment is configured to measure the number of blood cell aggregates passing through vascular branches in respective SLO images captured at different dates/times and subsequently display the change over time in the measured values from the different examination days and times.

Specifically, the image processing apparatus 10 according to the third embodiment obtains SLO images Dsif (f=1, 2, . . . , n−1), blood vessel images Vsif, measurement target vascular branches, and data regarding measured values for the number of blood cell aggregates from past examination days and times. Then, the image processing apparatus 10 registers the SLO images Dsin that are obtained at the present time and the SLO images Dsif from past examination days and times. Next, the image processing apparatus 10 uses the same method used in the first embodiment on the SLO images Dsin to measure the number of blood cell aggregates in the same vascular branches that were measurement targets in the past SLO images Dsif. Then, the image processing apparatus 10 displays a graph by registering the measured values in a time series with a normal value range attached.

The configuration of devices that are connected to the image processing apparatus 10 and the functional blocks of the image processing apparatus 10 according to the third embodiment are similar to those of the second embodiment. An image processing operation performed according to the third embodiment will be described below with reference to FIG. 10. Note that steps S1030, S1070, S1080, and S1090 are similar to those in the second embodiment and therefore the description will not be repeated here. Also, in the third embodiment, since step S1030 is processing for generating an image to be used secondarily as reference information and is not required for measurement, the actual processing of step S1030 may be skipped.

Note that when the SLO images or the fixation target positions are obtained at different magnifications, different imaging positions, or different examination days/times, they are expressed as Dsif and Fsif respectively. That is to say, s is a variable indicating magnification, i is a variable indicating imaging position number, f is a variable indicating examination day/time, and they are expressed as s=1, 2, . . . , smax, i=1, 2, . . . , imax, and f=1, 2, . . . , fmax. Here, as s increases, the imaging magnification increases (angle of view decreases). Also, the smaller f is, the further in the past the examination date/time is.

Step S1010

The image obtaining unit 110 makes a request to the data server 40 to transfer data for the past SLO images Dsif (f=1, 2, . . . , n−1), the fixation target positions Fsif, pulse data corresponding to the SLO images Dsif, the blood vessel images Vsif, the registration parameter values, the measurement target vascular branch positions, the positions of blood cell aggregates in the measurement target vascular branches, and measured values for the numbers of blood cell aggregates. The image processing apparatus 10 stores the data transferred by the data server 40 in response to the request in the storage unit 130. In the present embodiment, n=6 (i.e., the SLO images Dsi1 to Dsi5 are obtained as the past SLO images).

Next, the image obtaining unit 110 makes a request to the SLO imaging apparatus 20 to obtain the SLO images Dsin and the fixation target positions Fsin. In the present embodiment, a fixation target position F1ln is set on the macular fovea, fixation target positions F2in are set on the foveal and parafoveal regions, and a low-magnification SLO image D1ln and high-magnification SLO images D2in are obtained from the SLO imaging apparatus 20. Also, the pulse data obtaining unit 120 makes a request to the pulse data obtaining apparatus 50 to acquire the pulse data corresponding to the SLO images Dsin and acquires the pulse data from the pulse data obtaining apparatus 50.

Step S1020

The registration unit 144 determines the relative positions of the SLO images D2if on the SLO images D1lf (f=1, 2, . . . , n) by registering the SLO images D1lf and the SLO images D2if using a procedure similar to that in the second embodiment. A composite image of the SLO images D2if is generated using the information regarding the relative positions of the SLO images D2if on the SLO images D1lf.

Next, the SLO images D1ln and the SLO images D1lf (f=1, 2, . . . , n−1) from past examinations are registered. Furthermore, the relative positions of the SLO images D2if with respect to the SLO images D2in are obtained using the relative positions of the SLO images D1ln with respect to the SLO images D2in, the relative positions of the SLO images D1lf with respect to the SLO images D1ln, and the relative positions of the SLO images D2if with respect to the SLO images D1lf. Note that the registration of the SLO images D2in and the SLO images D2if may be performed directly. Here, the registration unit 144 obtains the fixation target position coordinates for the SLO images from the storage unit 130 and uses those fixation target position coordinates to set a search start point for registering the SLO images D2in with the SLO images D11n, the SLO images D11n with the reference images D11f, and D11f with D2if.

Any suitable method can be used as the registration method, and in the present embodiment, registration is first performed using Affine conversion as a general registration. Next, thorough registration is performed using FFD (Free Form Deformation), which is a non-rigid registration method. Although a correlation coefficient is used as the degree of image similarity in all registrations, the present invention is of course not limited to this, and any publicly-known degree of image similarity may be used. According to the description above, pixels of the SLO images D11n or D2in from the most recent examination are associated with pixels of the SLO images D11f or D2if from past examinations. Note that the registration performed by the registration unit 144 is not limited to a registration that is based on the above-mentioned degree of similarity between pixel values and a vascular region specified by the specification unit 141 may be used to perform registration of characteristic bases. Also, the present embodiment described a case of registering the positions of past examination images with respect to the SLO images D11n or D2in from the most recent examination, but the SLO images D11f or D2if from any examination date/time may be used to register the other SLO images. For example, if a reference image such as that described in step S1050 has been set, the reference image may be used to register the SLO images from other examination dates/times.

Step S1040

The measurement position determination unit 145 determines a vascular branch that is to be the target for measuring the number of blood cell aggregates. In the present embodiment, the measurement positions in the SLO images D2in are determined using the data regarding the measurement positions in the past examination images D2if that was obtained in step S1010, and the data regarding the relative positions of the SLO images D2if and the SLO images D2in that was obtained in step S1020. In other words, pixels in the SLO images D2in that correspond to the pixels of the vascular branches that were measured using the SLO images D2if are specified as the measurement target vascular branch regions.

Step S1050

The measurement unit 142 measures the number of blood cell aggregates in the vascular branch determined in step S1040. The measurement processing is similar to that of the second embodiment, and therefore the detailed description will not be repeated here.

Also, the measurement unit 142 calculates the difference between "measured values in the examination images (SLO images)" and their corresponding "measured values in the reference examination images". An image from any examination date/time can be set as the reference image, and in the present embodiment, the composite image of the SLO images D2i1 is set as the reference image. The difference between baselines is calculated using the values of a measured value map corresponding to the reference image as a baseline. This kind of index is not likely to be influenced by variation caused by sites within a normal value range or variation caused by individual differences, and therefore the change over time in the measured values can be understood with greater acuity.

Step S1060

The display control unit 143 displays the measured values for the number of blood cell aggregates that were obtained in step S1050, and a diagram generated based on those measured values on the monitor 305.

Figure 12C:
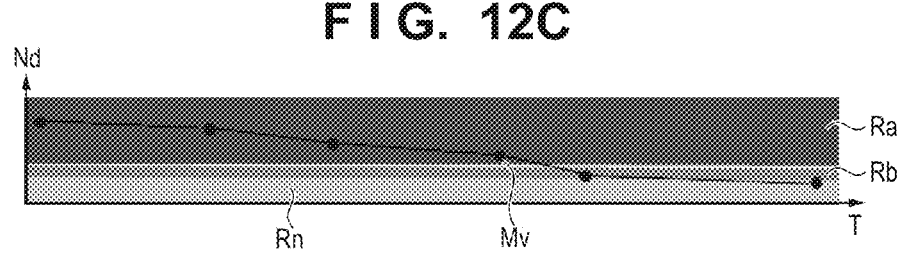

In the present embodiment, as the graph indicating the change over time in the number of blood cell aggregates with respect to the vascular branch designated by a user, the display control unit 143 displays a graph (FIG. 12C) in which a normal value range is plotted along with the examination date/time (T) on the horizontal axis and the blood cell aggregate number (Nd) on the vertical axis. In FIG. 12C, My indicates a measured value, Ra indicates the abnormal value range, Rb indicates the border between the abnormal value range and the normal value range, and Rn indicates the normal value range. Note that the horizontal axis may indicate the age of the examination subject. Accordingly, the effects of medical treatment (administration of medication) can be checked due to the measured numbers of blood cell aggregates and a normal value range over multiple dates/times after treatment (administration of medication) for example being displayed as the graph. Note that this graph of change over time is a graph displaying the change over time in the average values of the number of blood cell aggregates with respect to multiple measurement target vascular branches. Needless to say, the change over time in the measured number of blood cell aggregates with respect to a single vascular branch may be displayed as the graph as well.

Figure 12D:
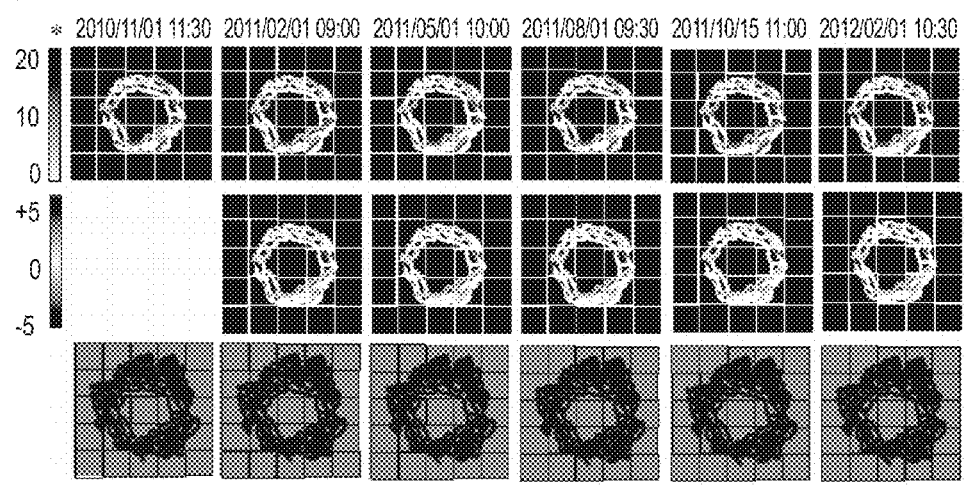

It is also possible to display the maps of the numbers of blood cell aggregates (in the measurement target vascular branch) in the composite SLO images D2if (f=1, 2, . . . , n) at the examination dates/times by arranging them in a line in order of examination date/time as shown in FIG. 12D. Accordingly, the change over time in the distribution of the numbers of blood cell aggregates can be listed and understood.

In FIG. 12D, maps of measured values for the numbers of blood cell aggregates are registered in order of examination date/time in the top row, and maps of the differences between a baseline and the measured values are in the center row. Composite maps obtained by compositing the SLO images D2if as described in step S1060 of the second embodiment are in the bottom row. Note that if composite maps of moving images are registered in order of examination date/time and displayed, it is desirable to perform display processing after performing processing for making the cycle values of the phase for the pulse data and the reference image at the time of starting moving image playback the same as that in the reference image.

Note that the examination dates/times are displayed above the upper row of measured value maps in FIG. 12D and adding a mark (an asterisk is used in the present example) to the reference examination date/time will facilitate an understanding of which measured value map is the baseline.

Note that the display of the measured values for the numbers of blood cell aggregates in the present embodiment is not limited to this, and any type of display is possible as long as it is based on the measured values for the numbers of blood cell aggregates. For example, maps of the deviations calculated in the second embodiment may be registered in order of examination date/time and displayed.

According to the above-described configuration, the image processing apparatus 10 measures the numbers of blood cell aggregates passing through vascular branches in respective SLO images captured at different dates/times and thereafter displays the change over time in the measured values at the different examination dates/times. This allows non-invasive measurement and display of the change over time in blood fluidity at different examination dates/times.

Fourth Embodiment

The image processing apparatus 10 according to a fourth embodiment is configured to set the focus position to the inner layer of the retina, directly detect erythrocytes in the captured SLO images Dsi, subsequently determine blood cell aggregates based on the distances between the erythrocytes, and measure the number of blood cell aggregates between vascular bifurcations.

Figure 13A:
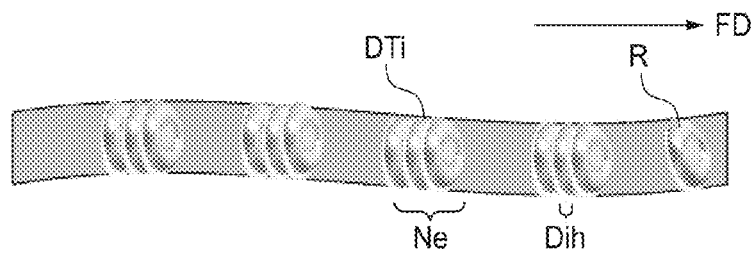
FIGS. 13A to 13C are diagrams for describing the contents of image processing executed by the image processing apparatus according to the fourth embodiment.

In the first to third embodiments, the SLO images are captured with the focus position set to the proximity of the photoreceptors (B5 in FIG. 6A), and therefore the erythrocyte aggregates DTi were dark tails as shown in FIG. 6C, but in the present embodiment, the SLO images are captured with the focus position set to the retinal inner layers (B2 to B4 in FIG. 6A), and therefore the erythrocytes R and the erythrocyte aggregates DTi are high-luminance regions as shown in FIG. 13A. Therefore, the image processing apparatus 10 specifies the vascular regions in the SLO images Dsi that were captured with the focus position set to the retinal inner layers, subsequently generates a spatiotemporal image using the vascular region, and detects a high-luminance path indicating the movement path of erythrocytes. Next, the image processing apparatus 10 detects blood cell aggregates based on the distances between the high-luminance paths and measures the number of detected blood cell aggregates.

The configuration of devices that are connected to the image processing apparatus 10 and the functional blocks of the image processing apparatus 10 according to the fourth embodiment are similar to those of the first embodiment (FIGS. 1 and 2). An image processing flow according to the fourth embodiment will be described below with reference to the flowchart in FIG. 10. Note that steps S1020, S1040, S1060, S1070, S1080, and S1090 are similar to those in the second embodiment and therefore the description will not be repeated here.

Step S1010

The image obtaining unit 110 makes a request to the SLO imaging apparatus 20 to obtain the SLO images Dsi and the fixation target positions Fsi. In the fourth embodiment, the focus position is set to the retinal inner layers (proximal to the retinal blood vessels), a low-magnification SLO image D1 is subsequently obtained with the fixation target position F1 set to the macular fovea, and high-magnification SLO images D2i are obtained with the fixation target positions F2i set to the foveal and parafoveal regions. Note that the method for setting the imaging position is not limited to this, and a setting of any position may be used.

The SLO imaging apparatus 20 obtains the SLO images D1 and D2i whose focus positions were set to the retinal inner layer and the fixation target positions F1 and F2i in response to the obtainment request and transmits them. The image obtaining unit 110 receives the SLO images D1 and D2i and the fixation target positions F1 and F2i from the SLO imaging apparatus 20 via the LAN 30 and stores them in the storage unit 130. Note that in the present embodiment, the SLO images D1 and D2i are moving images whose frames have been registered. Also, the obtainment of the pulse data is similar to the case of the first and second embodiments, and therefore the description will not be repeated here.

Step S1030

Similarly to the cases of the first and second embodiments, the specification unit 141 specifies the vascular region as the blood cell component movement range in the SLO image D2i. Note that at the time of binarization, binarization is performed using a threshold value Tv2 that is different from the threshold value Tv.

Step S1050

Figure 13B:
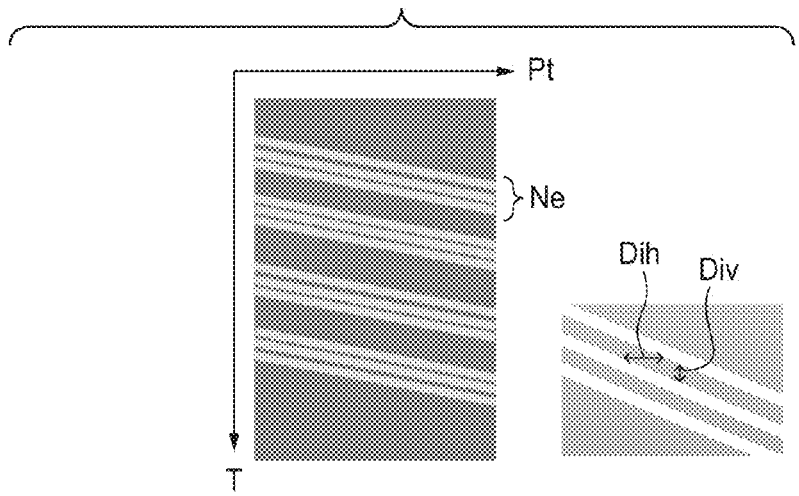

First, the specification unit 141 specifies the erythrocytes R in the vascular regions. In the present embodiment, a spatiotemporal image is generated using the vascular branches that were determined in step S1040, and a filter for enhancing linear structures (FIG. 13B) is applied to the spatiotemporal image, whereafter binarization is performed, and thereby a high-luminance path region, or in other words, the erythrocyte region R is detected.

Note that the method for specifying the erythrocytes is not limited to the method described above, and any publicly-known regional segmentation may be used for specification. For example, in the SLO images that were captured with the focus position set to the inner retinal layers, the erythrocytes R are rendered as small circular high-luminance regions R as shown in FIG. 13A. Therefore, by performing Fourier transformation directly on the vascular regions in the SLO images, removing high-frequency components, and subsequently performing inverse transformation, binarizing the resulting image using a threshold value Te, and shaping the resulting binary image using contraction/expansion processing, the erythrocytes R may be specified without the spatiotemporal image being generated.

Next, the specification unit 141 specifies the erythrocyte aggregates DTi based on the specified erythrocytes R. In the present embodiment, the detected erythrocytes R are labeled in the spatiotemporal image (FIG. 13B) that was used at the time of specifying the erythrocytes R. Next, if the distance (distance Dih between erythrocytes in horizontal direction or distance Div between erythrocytes in vertical direction) between erythrocytes (high-luminance paths) is less than a threshold value Tih or Tiv, it is determined that the erythrocytes have aggregated and the same label is allocated to both erythrocytes. Furthermore, if the number of erythrocytes (Ne) with the same label in a cluster of erythrocytes is at or above a threshold value Tn, the cluster of erythrocytes is specified as an erythrocyte aggregate DTi. Note that if the sum of the sizes (e.g., the total lengths in the vertical direction or the horizontal direction of the high-luminance paths to which the same label has been attached in the spatiotemporal image) of erythrocytes with the same label is at or above a threshold value Tn2, it may be specified as an erythrocyte aggregate DTi.

Figure 13C:
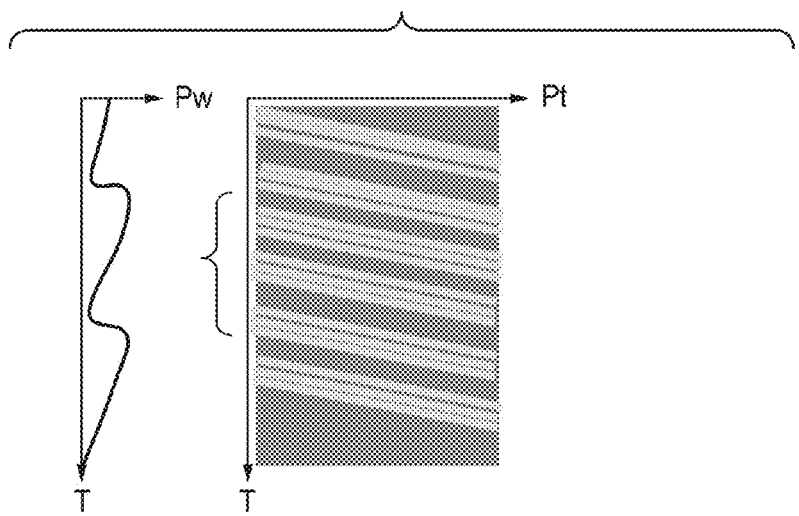

Furthermore, the number of erythrocyte aggregates in the vascular branches (in the SLO images D2in) that were specified by the measurement unit 142 in step S1040 is measured (FIG. 13C). Note that the measurement processing is similar to that of the first embodiment and the second embodiment (FIGS. 7E and 7F), and therefore the detailed description will not be repeated here.

According to the above-described configuration, the image processing apparatus 10 directly detects erythrocytes in SLO images Dsi that were captured with the focus position set to the retinal inner layer, and thereafter determines the blood cell aggregates based on the distance between the erythrocytes and measures the number of blood cell aggregates. Accordingly, blood fluidity can be measured non-invasively based on the number of blood cell aggregates.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiments of the present invention, and by a method performed by the computer of the system or apparatus by, for example, reading out and executing the computer executable instructions from the storage medium to perform the functions of one or more of the above-described embodiments. The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The above-described processing method can be applied to a portion other than a retina. For example, the above-described processing method can be applied to anterior eye part.

This application claims the benefit of Japanese Patent Application No. 2013-040040, filed Feb. 28, 2013, which is hereby incorporated by reference herein in its entirety.

What is claimed is:

1. An information processing apparatus comprising:
   an image obtaining unit configured to obtain a moving image of an eye area;
   a vascular region specifying unit configured to specify a vascular region in the obtained moving image;
   a detecting unit configured to detect at least one blood cell aggregate in the specified vascular region by using luminance value information of the specified vascular region; and
   a determining unit configured to determine the number of the detected at least one blood cell aggregate.

2. The apparatus according to claim 1, wherein the detecting unit detects, as the at least one blood cell aggregate, a location that (a) is adjacent to a region having a luminance value that is higher than a threshold value and (b) has a luminance value that is lower than a threshold value in the specified vascular region.

3. The apparatus according to claim 1, further comprising:
   an information obtaining unit configured to obtain the vascular diameters of a plurality of vascular branches that include a plurality of vascular bifurcations in the obtained moving image,
   wherein the detecting unit detects the at least one blood cell aggregate in a vascular branch having a vascular diameter that is within a predetermined range among the plurality of vascular branches.

4. The apparatus according to claim 3, further comprising:
   a vascular branch specifying unit configured to specify the plurality of vascular branches, one vascular branch being a region that includes two neighboring vascular bifurcations among the plurality of vascular bifurcations and a blood vessel between the two vascular bifurcations,
   wherein the information obtaining unit obtains the vascular diameters of the specified plurality of vascular branches.

5. The apparatus according to claim 1, further comprising:
   a display control unit configured to, on a display unit, display a distribution of at least one of a determined value based on the number of the at least one blood cell aggregate determined by the determining unit, and the difference between the determined value and a statistical value.

6. The apparatus according to claim 5, wherein the display control unit displays the determined value for the number of the at least one blood cell aggregate and a normal value range on the display unit.

7. The apparatus according to claim 5, wherein the display control unit makes a distinction between a blood vessel that does not include the at least one blood cell aggregate and a blood vessel that includes the at least one blood cell aggregate, and performs display based on the distinction.

8. The apparatus according to claim 1, further comprising:
   a display control unit configured to display change over time in the measured values for the number of the at least one blood cell aggregate in images that were obtained at different examination dates and times.

9. The apparatus according to claim 1, wherein the determining unit calculates the number of the at least one blood cell aggregate based on a plurality of determined values that were determined at times at which the phases of heartbeat or pulse wave data resemble each other.

10. The apparatus according to claim 9, wherein reliability degree for the calculated number of the at least one blood cell aggregate is calculated based on a statistical value for the plurality of determined values.

11. The apparatus according to claim 1, wherein the determining unit further performs at least one of:
   calculating an index based on at least one of the sum of the lengths of blood vessels that include the at least one blood cell aggregate, and the sum of the length of blood vessels that do not include the at least one blood cell aggregate, and
   calculating at least one of a percentage of the total lengths of blood vessels that include or do not include the at least one blood cell aggregate with respect to the total lengths of determination target blood vessels, and a value obtained by dividing the total lengths of blood vessels that include or do not include at least one blood cell aggregate by the area of a region of interest.

12. The apparatus according to claim 1, wherein the detecting unit detects the at least one blood cell aggregate based on a luminance value that is less than a first threshold value in the specified vascular region, and
   wherein the detecting unit detects, as the at least one blood cell aggregate, a location that is adjacent to a region having a luminance value that is higher than a second threshold value that is different from the first threshold value, the location having a luminance value that is lower than the first threshold value.

13. The apparatus according to claim 1, wherein the detecting unit detects the at least one blood cell aggregate from the moving image based on a distance between detected blood cells.

14. An information processing method comprising:
   obtaining a moving image of an eye area;
   specifying a vascular region in the obtained moving image;

detecting at least one blood cell aggregate in the specified vascular region by using luminance value information of the specified vascular region; and determining the number of the detected at least one blood cell aggregate.

15. The method according to claim 14, wherein in the detecting, a location that (a) is adjacent to a region having a luminance value that is higher than a threshold value and (b) has a luminance value that is lower than a threshold value in the specified vascular region is determined as the at least one blood cell aggregate.

16. The method according to claim 14, wherein in the detecting, the at least one blood cell aggregate is detected based on a luminance value that is below a first threshold value in the specified vascular region, and wherein in the detecting, a location that (a) is adjacent to a region having a luminance value that exceeds a second threshold value that is different from the first threshold value and (b) has a luminance value that is lower than the first threshold value is detected as the at least one blood cell aggregate.

17. A non-transitory computer-readable storage medium storing a program for causing a computer to execute a method comprising:

obtaining a moving image of an eye area;

specifying a vascular region in the obtained moving image;

detecting at least one blood cell aggregate in the specified vascular region by using luminance value information of the specified vascular region; and determining the number of the detected at least one blood cell aggregate.

18. The medium according to claim 17, wherein in the detecting, the at least one blood cell aggregate is detected based on a luminance value that is below a first threshold value in the specified vascular region, and wherein in the detecting, a location that (a) is adjacent to a region having a luminance value that exceeds a second threshold value that is different from the first threshold value and (b) has a luminance value that is lower than the first threshold value is detected as the at least one blood cell aggregate.

\* \* \* \* \*